United States Patent [19]

Brown et al.

[11] Patent Number: 5,597,582
[45] Date of Patent: Jan. 28, 1997

[54] ORAL GEL CAPSULE FORMULATION OF 1,2,4-BENZOTRIAZINE OXIDES

[75] Inventors: Stephen Brown, Northumberland; Ross Blundell, Newcastle upon Tyne, both of England

[73] Assignee: Sanofi, Paris Cedex, France

[21] Appl. No.: 527,233

[22] Filed: Sep. 12, 1995

[51] Int. Cl.⁶ .................................................. A61K 9/48
[52] U.S. Cl. .......................... 424/456; 424/451; 424/455
[58] Field of Search ................................... 424/451, 455, 424/456

[56] References Cited

U.S. PATENT DOCUMENTS 5,484,612  1/1996  Brown ...................................... 424/649

Primary Examiner—James M. Spear
Attorney, Agent, or Firm—William J. Davis; Paul E. Dupont; Imre Balogh

[57] ABSTRACT

Disclosed are anticancer tumor soft gelatin capsules comprising a 1,2,4-benzotriazine oxide and an oily excipient selected from the group consisting of soybean oil and fractionated coconut oil.

10 Claims, No Drawings

ORAL GEL CAPSULE FORMULATION OF 1,2,4-BENZOTRIAZINE OXIDES

BACKGROUND OF THE INVENTION

1. Field of the Invention

The present invention relates to the field of treatments for cancer tumors. More particularly, the present invention relates to treatment of cancer tumors with 1,2,4-benzotriazine oxides contained in an encapsulated suspension for oral administration.

2. Reported Developments

Encapsulated suspensions and solutions as carriers of pharmaceutical substances are known in the prior art. For example: U.S. Pat. No. 4,701,327 discloses etoposide soft capsules comprising soft gelatin shells enclosing an etoposide solution therein; European Patent Specification, Publ. No. 0 341,584 B1 discloses a soft capsular preparation comprising sodium picosulfate in a polyethylene glycol solution; and G. B. Patent Application No. 2,229,094A discloses a gelatin capsule consisting of a fatty acid glyceride and/or mineral oil or paraffin as a carrier for ranitidine.

Liquid fill of soft or hard gelatin capsules provide a useful and advantageous means of formulating drug substances and permit incorporation of the active ingredient in the form of a semi-solid, liquid or paste. In most soft gel capsules provided by the prior art, major objects include stability on shelf-life and absorption or bioavailability for efficacy.

In the field of cancer tumor treatment rapid and complete absorption of an anti-cancer drug is of the utmost importance so that a dose/time regiment can be instituted to successfully attack the tumor cells. For example, when increasing the toxicity of chemotherapy agents toward solid tumors is intended, a cytotoxicity enhancing compound is administered to the patient subsequent to which within a certain time-period the chemotherapy agent is administered in order for the drugs to have synergistic affect. Rapid and total absorption of the two drugs enables the practitioner to set the interval times of administration for obtaining maximum efficacy. Parenteral administration is more prevalent of anti-tumor drugs. Such administration is, however, not without pain, inconvenience and the high cost of administration by a practitioner. A convenient oral route of delivery would eliminate these drawbacks in the treatment of cancer tumors.

The present invention has as its objective the provision of a capsule formulated of a 1,2,4-benzotriazine oxide from which the 1,2,4-benzotriazine oxide absorbs rapidly and completely when administered to the patient. In addition, the formulation is stable on shelf-life.

1,2,4-Benzotriazine oxides are known compounds. U.S. Pat. No. 3,980,779 discloses 3-amino-1,2,4-benzotriazine-1,4-di-oxide compositions having the formula

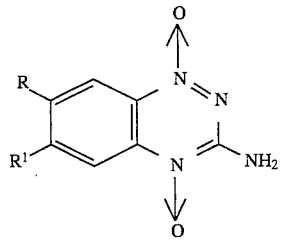

wherein one of R and $R^1$ is hydrogen, halogen, lower alkyl, halo (lower alkyl), lower alkoxy, carbamoyl, sulfonamido, carboxy or carbo (lower alkoxy) and the other of R and $R^1$ is halogeno, lower alkyl, halo (lower alkyl), lower alkoxy, carbamoyl, sulfonamido, carboxy or carbo (lower alkoxy), as antimicrobial composition used to promote livestock growth.

U.S. Pat. No. 5,175,287 issued Dec. 29, 1992 discloses the use of 1,2,4-benzotriazine oxides in conjunction with radiation for treatment of tumors. The 1,2,4-benzotriazine oxides sensitize the tumor cells to radiation and make them more amenable to this treatment modality.

Holden et al (1992) "Enhancement of Alkylating Agent Activity by SR-4233 in the FSaIIC Murine Fibrosarcoma" JNCI 84: 187–193 discloses the use of SR-4233, namely 3-amino-1,2,4-benzotriazine-1,4-dioxide, also known and hereinafter sometimes referred to as tirapazamine, in combination with an antitumor alkylating agent. The four antitumor alkylating agents, cisplatin, cyclophosphamide, carmustine and melphalan, were each tested to examine the ability of tirapazamine to overcome the resistance of hypoxic tumor cells to antitumor alkylating agents. Tirapazamine was tested alone and in combination with varying amounts of each of the antitumor alkylating agents. When SR-4233 was administered just before single-dose treatment with cyclophosphamide, carmustine or melphalan marked dose enhancement leading to synergistic cytotoxic effects on tumor cells was observed.

International Application No. PCT/US89/01037 discloses 1,2,4-benzotriazine oxides as radiosensitizers and selective cytotoxic agents. Other related patents include: U.S. Pat. Nos. 3,868,372 and 4,001,410 which disclose the preparation of 1,2,4-benzotriazine oxides; and U.S. Pat. Nos. 3,991,189 and 3,957,799 which disclose derivatives of 1,2,4-benzotriazine oxides.

SUMMARY OF THE INVENTION

The present invention provides a capsule formulation comprising: a fractionated coconut oil formulation or a soybean oil formulation as vehicles admixed with a compound of the formula (I)

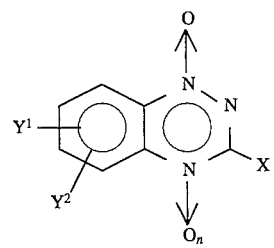

wherein

X is H; hydrocarbyl (1–4C); hydrocarbyl (1–4C) substituted with OH, $NH_2$, NHR or NRR; halogen; OH; alkoxy (1–4C); $NH_2$; NHR or NRR; wherein each R is independently selected from lower alkyl (1–4C) and lower acyl (1–4C) and lower alkyl (1–4C) and lower acyl (1–4C) substituted with OH, $NH_2$, alkyl (1–4C) secondary and dialkyl (1–4C) tertiary amino groups, alkoxy (1–4C) or halogen; and when X is NRR, both R's taken together directly or through a bridge oxygen to form a morpholino ring, pyrrolidino ring or piperidino ring;

n is 0 or 1; and $Y^1$ and $Y^2$ are independently either H; nitro; halogen; hydrocarbyl (1–14C) including cyclic and unsaturated hydrocarbyl, optionally substituted with 1 or 2 substituents selected from the group consisting of halogen, hydroxy, epoxy, alkoxy (1–4C), alkylthio (1–4C), primary amino ($NH_2$), alkyl (1–4C) secondary amino, dialkyl (1–4C) tertiary amino, dialkyl (1–4C) tertiary amino where the two alkyls are linked together to produce a morpholino, pyrrolidino or piperidino, acyloxy (1–4C), acylamido (1–4C) and thio analogs thereof, acetylaminoalkyl (1–4C), carboxy, alkoxycarbonyl (1–4C), carbamyl, alkylcarbamyl (1–4C), alkylsulfonyl (1–4C) or alkylphosphonyl (1–4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1–4C) which may be substituted with OH, $NH_2$, alkyl (1–4C) secondary amino, dialkyl (1–4C) tertiary amino, morpholino, pyrrolidino, piperidino, alkoxy (1–4C), or halogen substituents, or pharmacologically acceptable salt of said compound.

The preferred compound used in the present invention is 3-amino-1,2,4-benzotriazine (tirapazamine).

The present invention is also directed to a method of cancer tumor treatment comprising: administering to a mammal in need of such treatment an effective amount of the oral formulation as defined herein.

The oral formulation is contained in a soft or hard gelatin capsule. The total weight content of the capsule ranges from 200 to 2000 mg and comprises;

of from 5 to 50% w/w of a compound of the formula (I);

of from 50 to 95% w/w of an oily excipient of fractionated coconut oil or soybean oil;

of from 0 to 30% w/w and preferably of from about 10 to 20% w/w of a single or combination of a viscosity modifier(s) examples of which are hydrogenated vegetable oils, yellow wax, and glycerol monosterate; and of from 0 to 10% w/w and preferably of from about 2 to 8% w/w of a single or combination of pharmaceutically acceptable surface active agent examples of which are sorbitan monolaurate, polysorbate 20, 40, 60 and 80, lecithin and potoxamer 124, 188, 237, 338 and 407.

DETAILED DESCRIPTION OF THE INVENTION

The Antitumor Agents

The present invention provides a composition and a method for treating mammalian cancer tumors, including human cancer tumors, particularly solid tumors. In this aspect of the invention, an effective amount of a compound having Formula I, as defined herein, contained in a soft gel capsule, is administered to a mammal having a cancer tumor and in need of such treatment from about one half hour to about twenty-four hours before an effective amount of a chemotherapy agent to which the tumor is susceptible is administered to the mammal. Formula I and testing of a compound is described in U.S. application Ser. No. 125,609 filed on Sep. 22, 1993 U.S. Pat. No. 5,484,612, the disclosure of which in its entirety is incorporated herein by reference.

As used herein, susceptibility of a tumor to a chemotherapy agent refers to a chemotherapy agent that is capable of exerting a therapeutic effect on a tumor by any mechanism such as by killing tumor cells, reducing cell proliferation or reducing the size of the tumor. Also as used herein, effective amount of the compound of Formula I as defined herein, refers to amounts capable of killing tumor cells or capable of killing tumor cell in conjunction with a chemotherapy agent. An effective amount of a chemotherapy agent refers to an amount of the chemotherapy agent capable of killing cancer cells or otherwise producing a therapeutic effect such as by reducing tumor size or slowing tumor cell growth and proliferation.

The Gel Capsule Carrier of the Antitumor Agents

In the preparation of the soft gel capsules of the present invention extensive studies were conducted to provide characteristics in the soft gel capsules that will render the same stable and rapidly absorbable. Vehicles which appeared suitable included:

Fractionated Coconut Oil

Peanut Oil

Soybean Oil

PEG 400.

The initial preparations were made as follows: 1.0 g of tirapazamine was added to 9.0 g of each of the vehicles and placed in screw capped glass vials for physical and chemical stability evaluation.

Physical stability: Drug/vehicle mixes (5 ml in screw capped glass vials) were temperature cycled (5° C.–40° C.) every 24 hours and monitored for particle size at 0, 1, 2 and 4 weeks.

Chemical stability: Drug/vehicle mixes (5 ml in screw capped glass vials) were stored at 70° C. for 4 weeks. Samples showing minimal or no changes in physical stability (particle size increase) were analyzed for chemical stability.

The physical/chemical studies indicated that fractionated coconut oil and soybean oil could be suitable for further experimentation, while peanut oil and PEG 400 were found to be unacceptable. Chemical stability data is shown in Table I. Accordingly, fractionated coconut oil and soybean oil formulations (examples 1 and 2) containing surfactants were prepared using a theoretically determined amount of the drug required for efficacy:

1. The required amount of drug was weighed.

2. The oil and emulsifier mixture was added to the drug.

3. The fatmix (Yellow Wax 20%+Hydrogenated Vegetable Oil 80% w/w) was melted (around 40° C.) and added to stage 2.

4. The mix was homogenized on an Ultra Turrax homogenizer for 3×1 minute.

TABLE I

Percentage Estimated Total Inhomogeneity (ETI) by Weight As Determined by Liquid Chromatography for Tirapazamine/Vehicle Mixes After 6 Weeks at 70° C.

| Vehicle | Initial | 70° C./4 Weeks A | B |
|---|---|---|---|
| Fractionated Coconut Oil | 0.30 | 0.26 | 0.21 |
| Peanut Oil | 0.24 | 1.92 | 1.94 |
| Soybean Oil | 0.27 | 1.91 | 1.90 |
| PEG 400 | 0.24 | 19.11 | 19.13 |

EXAMPLE 1

| | |
|---|---|
| Tirapazamine | 50 mg |
| Fractionated Coconut Oil | 269 mg |
| Sorbitan Menotaurate | 13 mg |
| Yellow Wax | 25.8 mg |
| Hydrogenated Vegetable Oil | 103.2 mg |
| TOTAL | 441 mg |

EXAMPLE 2

| | |
|---|---|
| Tirapazamine | 50 mg |
| Soybean Oil | 245 mg |
| Lecithin | 5 mg |
| Yellow Wax | 25.2 mg |
| Hydrogenated Vegetable Oil | 101.8 mg |
| TOTAL | 427 mg |

Particle size and chemical analysis were conducted on formulation examples 1 and 2. The results are shown in Table II and III.

TABLE II

Mean Particle Size (μm) as Determined by Laser Diffraction of Formation Examples 1 and 2 After 4 Weeks Storage at 70° C.

| | Particle Size μm | |
|---|---|---|
| Time Point (Weeks) | Example 4 | Example 5 |
| 0 | 90.8 | 143.1 |
| 1 | 113.2 | 120.2 |
| 2 | 133.9 | 147.1 |
| 4 | 136.7 | 149.7 |

Both formulations were stable with regards to ETI for 4 weeks at 5° C./40° C. cycle.

TABLE III

Percent Estimated Total Inhomogeneity (ETI) by Weight as Determined by Liquid Chromatography for Formulation Examples 1 and 2 After Storage at 70° C. and Cycled between 5° C. and 40° C. for 4 Weeks

| Formulation | Initial | 70° C. 4 Weeks | 5–40° C. 4 Weeks |
|---|---|---|---|
| Example 1 | 0.27 | 3.41 | 0.15 |
| Example 2 | 0.20 | 3.11 | 0.16 |

Particle size of the drug did not significantly change over 4 weeks with either the fractionated coconut oil or the soybean oil formulations. Both formulations were chemically stable for 4 weeks when stored at a 5° C./40° C. cycle, though significant degradation was observed after 4 weeks at 70° C.

The prepared capsule size had a target fill weight of 280 mg (±10%) and therefore adjustment of formulation examples 1 and 2 was necessary. The resulting formulations are shown in examples 3 and 4.

EXAMPLE 3

| | |
|---|---|
| Tirapazamine | 50 mg |
| Fractionated Coconut Oil | 175.9 mg |
| Sorbitan monolaurate | 9.30 mg |
| Yellow Wax | 8.96 mg |
| Hydrogenated Vegetable Oil | 35.84 mg |
| TOTAL | 280 mg |

EXAMPLE 4

| | |
|---|---|
| Tirapazamine | 50 mg |
| Soybean Oil | 178.5 mg |
| Lecithin | 3.68 mg |
| Yellow Wax | 7.56 mg |
| Hydrogenated Vegetable Oil | 30.26 mg |
| TOTAL | 270 mg |

Chemical analysis of formation examples 3 and 4 was carried out over a period of 17 weeks and at various storage conditions. Results are shown in Table IV.

TABLE IV

Percent Estimated Total Inhomogeneity by Weight as Determined by Liquid Chromatography for Tirapazamine Formulation Examples 3 and 4 After Storage for 17 Weeks ETI Results of Fractionated Coconut Oil Formulation After 17 Weeks Storage Initial: 0.41

| | 1 Week | | 4 Week | | 17 Week | |
|---|---|---|---|---|---|---|
| Condition | A | B | A | B | A | B |
| 5° C. | | | | | 0.28 | 0.32 |
| 30° C. | 0.37 | 0.27 | 0.38 | 0.22 | 0.50 | 0.47 |
| 30° C./75% RH | 0.22 | 0.18 | 0.24 | 0.32 | 0.46 | 0.49 |
| 40° C. | 0.21 | 0.25 | 0.38 | 0.48 | 1.15 | 2.87 |

ETI Results of Soybean Oil Formulation After 17 Weeks Storage

Initial: 2.39

| | 17 Week | |
|---|---|---|
| Condition | A | B |
| 30° C. | 0.94 | 1.02 |
| 30/75% RH | 0.84 | 0.74 |
| 40° C. | 4.52 | 4.06 |

A and B indicate duplicate analysis

Both formulation examples 3 and 4 show significant degradation at 40° C. after 17 weeks. The soybean formulation shows some degradation at 30° C. whilst the fractionated coconut oil formulation does not.

The preferred formulation by unit dose/mg and physical and chemical stability is shown in formulation-example 5.

EXAMPLE 5

| | |
|---|---|
| Tirapazamine | 50 mg |
| Fractionated Coconut Oil | 175.9 mg |
| Sorbitan Monolaurate | 9.26 mg |
| Hydrogenated Vegetable Oil | 37 mg |
| Yellow Wax | 7.4 mg |
| TOTAL | 280 mg |

Formulation example 5 was manufactured on a 2.1 kg scale. The hydrogenated vegetable oil and yellow wax were weighed out into a container. The container was heated and the contents stirred until melted. The fractionated coconut oil and sorbitan monolaurate were thoroughly mixed and then introduced to the melted hydrogenated vegetable oil/yellow wax mix. The resulting mixture was warmed and stirred until a homogenous mix resulted. Tirapazamine was then introduced into the mix while stirring. The resulting suspension was homogenized.

Formulation example 5 showed good physical characteristics for filling into capsules. The paste demonstrated good shear thinning flow characteristics and did not separate after standing for 18 hours. This formulation was found to be processible on a soft gelatin capsule filling machine. Table V shows the "In Process" data taken during the manufacture of a 2.1 kg batch of formulation example 5. Table VI shows the "In Process" data taken during the filling of this suspension into soft gelatin capsules.

TABLE V

In Process Analysis of Suspension for Tirapazamine Soft Gelatin Capsule Manufacture (assay by UV)

| Sample Point | mg/280 | % of Claim 50 mg/280 mg |
|---|---|---|
| Top | 47.62 | 95.24 |
|  | 46.71 | 93.42 |
| Bottom | 48.22 | 96.44 |
|  | 48.65 | 97.30 |
| Mean | 47.80 | 95.60 |

TABLE VI

Analysis of in Process Samples Taken During the Filling of Tirapazamine Soft Gelatin Capsule Manufacture Assay by liquid chromatography (mean of 5 capsules) of capsules taken at start, middle and end of filling operation.

| Sample Point | mg/cap | % Theory | % RSD |
|---|---|---|---|
| Start | 50.12 | 100.2 | 2.18 |
| Middle | 50.67 | 101.3 | 0.70 |
| End | 48.77 | 97.5 | 0.98 |

% RSD = % relative standard deviation
Uniformity of weight (mean of 5) of capsules taken at start, middle and end of filling operation

| Sample Point | mg | Range/mg |
|---|---|---|
| Start | 284.97 | 278.09–288.19 |
| Middle | 286.09 | 285.14–286.87 |
| End | 282.03 | 278.71–284.41 |

Having described the invention with reference to its preferred embodiments, it is to be understood that modifications within the scope of the invention will be apparent to those skilled in the art.

What is claimed is:

1. A gelatin capsule comprising a gelatin shell having enclosed therein based on the total weight of content of from about 200 to about 2000 mg: of from about 5 to about 50% w/w of an anticancer compound of the formula

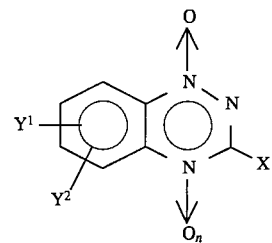

wherein

X is H; hydrocarbyl (1–4C); hydrocarbyl (1–4C) substituted with OH, $NH_2$, NHR or NRR; halogen; OH; alkoxy (1–4C); $NH_2$; NHR or NRR; wherein each R is independently selected from lower alkyl (1–4C) and lower acyl (1–4C) and lower alkyl (1–4C) and lower acyl (1–4C) substituted with OH, $NH_2$, alkyl (1–4C) secondary and dialkyl (1–4C) tertiary amino groups, alkoxy (1–4C) or halogen; and when X is NRR, both R's taken together directly or through a bridge oxygen to form a morpholino ring, pyrrolidino ring or piperidino ring;

n is 0 or 1; and $Y^1$ and $Y^2$ are independently either H; nitro; halogen; hydrocarbyl (1–14C) including cyclic and unsaturated hydrocarbyl, optionally substituted with 1 or 2 substituents selected from the group consisting of halogen, hydroxy, epoxy, alkoxy (1–4C), alkylthio (1–4C), primary amino ($NH_2$), alkyl (1–4C) secondary amino, dialkyl (1–4C) tertiary amino, dialkyl (1–4C) tertiary amino where the two alkyls are linked together to produce a morpholino, pyrrolidino or piperidino, acyloxy (1–4C), acylamido (1–4C) and thio analogs thereof, acetylaminoalkyl (1–4C), carboxy, alkoxycarbonyl (1–4C), carbamyl, alkylcarbamyl (1–4C), alkylsulfonyl (1–4C) or alkylphosphonyl (1–4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1–4C) which may be substituted with OH, $NH_2$, alkyl (1–4C) secondary amino, dialkyl (1–4C) tertiary amino, morpholino, pyrrolidino, piperidino, alkoxy (1–4C), or halogen substituents, or pharmacologically acceptable salt of said compound;

of from about 50 to about 95% w/w of an oily excipient selected from the group consisting of soybean oil and fractionated coconut oil;

of from about 0 to about 30% w/w of viscosity modifier; and of from about 0 to about 10% w/w of a pharmaceutically acceptable surface active agent.

2. The gelatin capsule of claim 1 wherein said anticancer tumor compound is 3-amino 1,2,4-benzotriazine.

3. The gelatin capsule of claim 1 wherein said anticancer tumor compound is present in said formulation in an amount of from about 10 to about 25% w/w.

4. The gelatin capsule of claim 1 wherein said oily excipient is present in said formulation in an amount of from about 60 to about 80% w/w.

5. The gelatin capsule of claim 1 wherein said viscosity modifier is selected from the group consisting of hydrogenated vegetable oils, and yellow wax and glycerol monostearate.

6. The gelatin capsule of claim 1 wherein said pharmaceutically acceptable surface active agent is selected from the group consisting of sorbitan monolaurate and lecithin.

7. The gelatin capsule of claim 1 wherein said viscosity modifier is present in said formulation in an amount of from about 10 to about 20% w/w.

8. The gelatin capsule of claim 1 wherein said surface active agent is present in said formulation in an amount of from about 2 to 8% w/w.

9. The gelatin capsule of claim 1 wherein said gelatin capsule is a soft gelatin capsule.

10. A method of treating cancer tumors in a mammal comprising: administering to said mammal in need of such treatment an effective amount of the gelatin capsule of claim 1.

* * * * *